US008252904B2

(12) United States Patent
Cheek et al.

(10) Patent No.: US 8,252,904 B2
(45) Date of Patent: Aug. 28, 2012

(54) GLYCODELIN MONOCLONAL ANTIBODIES AND METHODS FOR THEIR USE IN THE DETECTION OF OVARIAN CANCER

(75) Inventors: Robert L. Cheek, Mebane, NC (US); Eric P. Dixon, Cary, NC (US); Timothy J. Fischer, Raleigh, NC (US); John W. Groelke, Raleigh, NC (US); Steven L. Knapp, Apex, NC (US); Stephen G. Simkins, Fuquay-Varina, NC (US); Clark M. Whitehead, Apex, NC (US)

(73) Assignee: Tripath Imaging, Inc., Burlington, NC (US)

( * ) Notice: Subject to any disclaimer, the term of this patent is extended or adjusted under 35 U.S.C. 154(b) by 82 days.

(21) Appl. No.: 12/718,693

(22) Filed: Mar. 5, 2010

(65) Prior Publication Data

US 2010/0227343 A1   Sep. 9, 2010

Related U.S. Application Data

(60) Provisional application No. 61/158,159, filed on Mar. 6, 2009.

(51) Int. Cl.
C07K 16/00 (2006.01)
C07K 14/00 (2006.01)
C07K 5/00 (2006.01)
G01N 33/53 (2006.01)

(52) U.S. Cl. .............. 530/387.1; 530/387.9; 530/388.1; 530/330; 530/324; 530/395; 435/7.1

(58) Field of Classification Search ................. 435/7.94, 435/6.14; 530/387.1, 387.9
See application file for complete search history.

(56) References Cited

U.S. PATENT DOCUMENTS

| 2007/0212721 A1 | 9/2007 | Fischer et al. |
| 2008/0254048 A1 | 10/2008 | Cheek et al. |
| 2009/0068690 A1 | 3/2009 | Fischer et al. |
| 2009/0075307 A1 | 3/2009 | Fischer et al. |
| 2009/0087849 A1 | 4/2009 | Malinowski et al. |

FOREIGN PATENT DOCUMENTS

| DE | 198 07 389 A1 | 8/1999 |
| EP | 0 520 834 A2 | 12/1992 |
| WO | WO 02/45657 A2 | 6/2002 |
| WO | WO 02/071928 A2 * | 9/2002 |
| WO | WO 2007/090076 A2 | 8/2007 |

OTHER PUBLICATIONS

Cheek, R.L., et al., "HE4 and Glycodelin Are Serum Biomarkers for Ovarian Cancer," *Proceedings of 97th AACR Annual Meeting*, Apr. 1-5, 2006, Abstract No. 4504.
Chiu, P.C.N., et al., "Zona-Binding Inhibitory Factor-1 from Human Follicular Fluid is an Isoform of Glycodelin," *Biology of Reproduction*, 2003, pp. 365-372, vol. 69.
Dell, A., et al., "Structural Analysis of the Oligosaccharides Derived from Glycodelin, a Human Glycoprotein with Potent Immunosuppressive and Contraceptive Activities," *The Journal of Biological Chemistry*, 1995, pp. 24116-24126, vol. 270(41).
Koistinen, H., et al., "Glycodelin from Seminal Plasma Is a Differentially Glycosylated Form of Contraceptive Glycodelin-A," *Molecular Human Reproduction*, 1996, pp. 759-765, vol. 2(10).
Lapid, K., and N. Sharon, "Meet the Multifunctional and Sexy Glycoforms of Glycodelin," *Glycobiology*, 2006, pp. 39R-45R, vol. 16(3).

Mandelin, E., et al., "Glycodelin in Ovarian Serous Carcinoma: Association with Differentiation and Survival," *Cancer Research*, 2003, pp. 6258-6264, vol. 63.
Morris, H.R., et al., "Gender-Specific Glycosylation of Human Glycodelin Affects Its Contraceptive Activity," *The Journal of Biological Chemistry*, 1996, pp. 32159-32167, vol. 271(50).
Oehninger, S., et al., "Factors Affecting Fertilization: Endometrial Placental Protein 14 Reduces the Capacity of Human Spermatozoa to Bind to the Human Zona Pellucida," *Fertility and Sterility*, 1995, pp. 377-383, vol. 63(2).
Okamoto, N., et al., "Suppression by Human Placental Protein 14 of Natural Killer Cell Activity," *American Journal of Reproductive Immunology*, 1991, pp. 137-142, vol. 26.
Pockley, A.G., et al., "The Effect of Human Placental Protein 14 (PP14) on the Production of Interleukin-1 from Mitogenically Stimulated Mononuclear Cell Cultures," *Immunology*, 1990, pp. 277-281, vol. 69.
Rachmilewitz, J., et al., "Negative Regulation of T Cell Activation by Placental Protein 14 Is Mediated by the Tyrosine Phosphatase Receptor CD45," *The Journal of Biological Chemistry*, 2003, pp. 14059-14065, vol. 278(16). Seppala, M., et al., "Glycodelin: A Major Lipocalin Protein of the Reproductive Axis with Diverse Actions in Cell Recognition and Differentiation," *Endocrine Reviews*, 2002, pp. 401-430, vol. 23(4).
Seppala, M., et al., "Glycodelins," *Tumor Biology*, 1998, pp. 213-220, vol. 19.
Seppala, M., et al., "Glycosylation Related Actions of Glycodelin: Gamete, Cumulus Cell, Immune Cell and Clinical Associations," *Human Reproductive Update*, 2007, pp. 275-287, vol. 13(3).
Seppala, M., et al., "The Post-Menopausal Uterus: The Effect of Hormone Replacement Therapy on the Serum Levels of Secretory Endometrial Protein PP14/β-lactoglobulin Homologue," *Human Reproducton*, 1987, pp. 741-743, vol. 2(8).
Song, M., et al., "Angiogenic Role for Glycodelin in Tumorigenesis," *Proc Natl Acad Sci USA*, 2001, pp. 9265-9270, vol. 98(16).
Tse, J.Y.M., et al., "The Synthesis and Fate of Glycodelin in Human Ovary During Folliculogenesis," *Molecular Human Reproduction*, 2002, pp. 142-148, vol. 8(2).
Van Den Nieuwenhof, I.M., et al., "Recombinant Glycodelin Carrying the Same Type of Glycan Structures as Contraceptive Glycodelin-A Can Be Produced in Human Kidney 293 Cells But Not in Chinese Hamster Ovary Cells," *Eur. J. Biochem.*, 2000, pp. 4753-4762, vol. 267.

(Continued)

*Primary Examiner* — Peter J Reddig
*Assistant Examiner* — Yan Xiao
(74) *Attorney, Agent, or Firm* — Alston & Bird LLP

(57) ABSTRACT

Compositions and methods for diagnosing ovarian cancer in a patient and for identifying patients with an increased likelihood of having ovarian cancer are provided. The compositions include novel monoclonal antibodies, and variants and fragments thereof, that specifically bind to glycodelin. Monoclonal antibodies having the binding characteristics of a glycodelin antibody of the invention and monoclonal antibodies that bind to a glycodelin epitope of a disclosed antibody are further provided. Hybridoma cell lines that produce a glycodelin monoclonal antibody of the invention are also disclosed herein. The compositions find use in diagnostic methods as well as in screening methods for identifying patients having an increased likelihood of having ovarian cancer. Kits comprising one or more of the disclosed glycodelin monoclonal antibodies and for practicing the methods of the invention are further provided. Polypeptides comprising the amino acid sequence for a glycodelin epitope of a disclosed monoclonal glycodelin antibody and methods of using these polypeptides in the production of glycodelin antibodies are also encompassed by the present invention.

18 Claims, 2 Drawing Sheets

OTHER PUBLICATIONS

Vigne, J-L., et al., "Purification and Characterization of an Immunomodulatory Edometrial Protein, Glycodelin," *The Journal of Biological Chemistry*, 2001, pp. 17101-17105, vol. 276(20).

Warrenfeltz, S., et al., "Gene Expression Profiling of Epithelial Ovarian Tumours Correlated with Malignant Potential," *Molecular Cancer*, 2004, pp. 1-17, vol. 3(27).

Yaniv, E., et al., "Placental Protein 14 Regulates Selective B Cell Responses," *Cellular Immunology*, 2003, pp. 156-163, vol. 222.

Product Data Sheet for Glycodelin (N-20): sc-12289; Retrieved on Mar. 1, 2011 from the Internet: <URL: http://datasheets.scbt.com/sc-12289.pdf.

Baker, J.P., et al., "Characterization of Monoclonal Antibodies to Glycodelin Showing Clinical Utility in the Identification of Ovarian Cancer," *Proceedings of the American Association for Cancer Research Annual Meeting*, 2009, pp. 377, vol. 50.

Bischof, A., et al., "Measurement of Glycodelin A in Fluids of Benign Ovarian Cysts, Borderline Tumours and Malignant Ovarian Cancer," *Anticancer Research*, 2005, pp. 1639-1644, vol. 25(3A).

Havrilesky, L.J., et al., "Evaluation of Biomarker Panels for Early Stage Ovarian Cancer Detection and Monitoring for Disease Recurrence," *Gynecologic Oncology*, 2008, pp. 374-382, vol. 110(3).

Horowitz, I.R., et al., "Increased Glycodelin Levels in Gynecological Malignancies," *Int. J. Gyncol. Cancer*, 2001, pp. 173-179, vol. 11(3).

Jeschke, U., et al., "Development and Characterization of Monoclonal Antibodies for the Immunohistochemical Detection of Glycodelin A in Decidual, Endometrial and Gynaecological Tumour Tissues," *Histopathology*, 2006, pp. 394-406, vol. 48.

Jeschke, U., et al., "Development of Monoclonal and Polyclonal Antibodies and an ELISA for the Determination of Glycodelin in Human Serum, Amniotic Fluid and Cystic Fluid of Benign and Malignant Ovarian Tumors," *Anticancer Research*, 2005, pp. 1581-1590, vol. 25(3A).

Julkunen, M., et al., "Complete Amino Acid Sequence of Human Placental Protein 14: A Progesterone-Regulated Uterine Protein Homologous to β-Lactoglobulins," *Proc. Natl. Acad. Sci.*, 1998, pp. 8845-8849, vol. 85(23).

Kaemaeraeinen, I. L., et al., "Normal Human Ovary and Ovarian Tumors Express Glycodelin, a Glycoprotein with Immunosuppressive and Contraceptive Properties," *American Journal of Pathlogy*, 1996, pp. 1435-1443, vol. 148(5).

Karri, S-T., et al., "Characterization of Monoclonal Antibodies to Glycodelin and Recombinant Glycodelin," *The Histochemical Journal*, 2000, pp. 711-716, vol. 32(12).

Kunert-Keil, C., et al., "Immunolocalization of Glycodelin in the Genital Tract of Rats," *J. Mol. Hist.*, 2005, pp. 111-117, vol. 36.

Riittinen, L., et al., "Monoclonal Antibodies Against Endometrial Protein PP14 and Their use for Purification and Radioimmunoassay of PP14," *Journal of Immunological Methods*, 1991, pp. 85-90, vol. 136(1-2).

Scherbakova, L.A., et al., "Comparative Study of Enzyme-Linked Immunosorbent Assay and Radioimmunoassay Techniques in Determining Serum Placental Protein 14 Levels in Gynecologic Patients," *Tumor Biol.*, 1991, pp. 267-271, vol. 12(5).

Anonymous: "Human Glycodelin ELISA Kit," *Cusabio Biotech. Co., Ltd.*, URL:http://www.cusabio.cn/down/1231399788__2.pdf retrieved on Apr. 19, 2010.

* cited by examiner

SEQUENCE LISTING

```
<160> NUMBER OF SEQ ID NOS: 9

<210> SEQ ID NO 1
<211> LENGTH: 180
<212> TYPE: PRT
<213> ORGANISM: Homo sapiens

<400> SEQUENCE: 1

Met Leu Cys Leu Leu Leu Thr Leu Gly Val Ala Leu Val Cys Gly Val
 1               5                  10                  15

Pro Ala Met Asp Ile Pro Gln Thr Lys Gln Asp Leu Glu Leu Pro Lys
            20                  25                  30

Leu Ala Gly Thr Trp His Ser Met Ala Met Ala Thr Asn Asn Ile Ser
        35                  40                  45

Leu Met Ala Thr Leu Lys Ala Pro Leu Arg Val His Ile Thr Ser Leu
    50                  55                  60

Leu Pro Thr Pro Glu Asp Asn Leu Glu Ile Val Leu His Arg Trp Glu
65                  70                  75                  80

Asn Asn Ser Cys Val Glu Lys Lys Val Leu Gly Glu Lys Thr Glu Asn
                85                  90                  95

Pro Lys Lys Phe Lys Ile Asn Tyr Thr Val Ala Asn Glu Ala Thr Leu
            100                 105                 110

Leu Asp Thr Asp Tyr Asp Asn Phe Leu Phe Leu Cys Leu Gln Asp Thr
        115                 120                 125

Thr Thr Pro Ile Gln Ser Met Met Cys Gln Tyr Leu Ala Arg Val Leu
    130                 135                 140

Val Glu Asp Asp Glu Ile Met Gln Gly Phe Ile Arg Ala Phe Arg Pro
```

```
                145                 150                 155                 160
Leu Pro Arg His Leu Trp Tyr Leu Leu Asp Leu Lys Gln Met Glu Glu
                165                 170                 175

Pro Cys Arg Phe
        180

<210> SEQ ID NO 2
<211> LENGTH: 857
<212> TYPE: DNA
<213> ORGANISM: Homo sapiens

<400> SEQUENCE: 2
catccctctg gctccagagc tcagagccac ccacagccgc agccatgctg tgcctcctgc       60
tcaccctggg cgtggccctg gtctgtggtg tcccggccat ggacatcccc cagaccaagc      120
aggacctgga gctcccaaag ttggcaggga cctggcactc catggccatg gcgaccaaca      180
acatctccct catggcgaca ctgaaggccc tctgagggt ccacatcacc tcactgttgc       240
```
(corrected line 240 likely: acatctccct catggcgaca ctgaaggccc tctgagggt ccacatcacc tcactgttgc)
```
ccaccccga ggacaacctg gagatcgttc tgcacagatg ggagaacaac agctgtgttg        300
agaagaaggt ccttggagag aagactgaga tccaaagaa gttcaagatc aactatacgg        360
tggcgaacga ggccacgctg ctcgatactg actacgacaa tttcctgttt ctctgcctac      420
aggacaccac caccccatc cagagcatga tgtgccagta cctggccaga gtcctggtgg       480
aggacgatga gatcatgcag ggattcatca gggctttcag gcccctgccc aggcacctat      540
ggtacttgct ggacttgaaa cagatggaag agccgtgccg tttctaggtg agctcctgcc      600
tggtcctgcc tcctggctca cctccgcctc caggaagacc agactccac ccttccacac       660 ctccagagca gtgggacttc ctcctgccct ttcaaagaat aaccacagct cagaagacga      720
tgacgtggtc atctgtgtcg ccatcccctt cctgctgcac acctgcacca cggccatggg      780
gaggctgctc cctgggggca gagtctctgg cagaggttat taataaaccc ttggagcatg      840
aaaaaaaaaa aaaaaaa                                                     857

<210> SEQ ID NO 3
<211> LENGTH: 31
<212> TYPE: PRT
<213> ORGANISM: Artificial Sequence
<220> FEATURE:
<223> OTHER INFORMATION: Epitope sequence forglycodelin monoclonal
      antibody designated as 2G7.1

<400> SEQUENCE: 3

Ala Thr Leu Leu Asp Thr Asp Tyr Asp Asn Phe Leu Phe Leu Cys Leu
  1               5                  10                  15

Gln Asp Thr Thr Thr Pro Ile Gln Ser Met Met Cys Gln Tyr Leu
              20                  25                  30

<210> SEQ ID NO 4
<211> LENGTH: 190
<212> TYPE: PRT
<213> ORGANISM: Artificial Sequence
<220> FEATURE:
<223> OTHER INFORMATION: Glycodelin sequence fused to a small
      polypeptide linker and a carboxy-terminal hexahistidine tag
      (immunogenic polypeptide)

<400> SEQUENCE: 4

Met Leu Cys Leu Leu Leu Thr Leu Gly Val Ala Leu Val Cys Gly Val
  1               5                  10                  15

Pro Ala Met Asp Ile Pro Gln Thr Lys Gln Asp Leu Glu Leu Pro Lys
              20                  25                  30
```

```
Leu Ala Gly Thr Trp Arg Ser Met Ala Met Ala Thr Asn Asn Ile Ser
            35                  40                  45

Leu Met Ala Thr Leu Lys Ala Pro Leu Arg Val His Ile Thr Ser Leu
 50                  55                  60

Leu Pro Thr Pro Glu Asp Asn Leu Glu Ile Val Leu His Arg Trp Glu
 65                  70                  75                  80

Asn Asn Ser Cys Val Glu Lys Lys Val Leu Gly Glu Lys Thr Glu Asn
                 85                  90                  95

Pro Lys Lys Phe Lys Ile Asn Tyr Thr Val Ala Asn Glu Ala Thr Leu
                100                 105                 110

Leu Asp Thr Asp Tyr Asp Asn Phe Leu Phe Leu Cys Leu Gln Asp Thr
                115                 120                 125

Thr Thr Pro Ile Gln Ser Met Met Cys Gln Tyr Leu Ala Arg Val Leu
                130                 135                 140

Val Glu Asp Asp Glu Ile Met Gln Gly Phe Ile Arg Ala Phe Arg Pro
145                 150                 155                 160

Leu Pro Arg His Leu Trp Tyr Leu Leu Asp Leu Lys Gln Met Glu Glu
                165                 170                 175

Pro Cys Arg Phe Leu Glu Gly Gly His His His His His
                180                 185                 190

<210> SEQ ID NO 5
<211> LENGTH: 4
<212> TYPE: PRT
<213> ORGANISM: Artificial Sequence
<220> FEATURE:
<223> OTHER INFORMATION: Minimal epitope sequence of glycodelin
      monoclonal antibody designated as 2G7.1

<400> SEQUENCE: 5

Pro Ile Gln Ser
 1

<210> SEQ ID NO 6
<211> LENGTH: 4
<212> TYPE: PRT
<213> ORGANISM: Artificial Sequence
<220> FEATURE:
<223> OTHER INFORMATION: Part of full epitope sequence of glycodelin
      monoclonal antibody designated as 2G7.1

<400> SEQUENCE: 6

Arg Pro Leu Pro
 1

<210> SEQ ID NO 7
<211> LENGTH: 9
<212> TYPE: PRT
<213> ORGANISM: Artificial Sequence
<220> FEATURE:
<223> OTHER INFORMATION: Part of full epitope sequence of glycodelin
      monoclonal antibody designated as 2G7.1

<400> SEQUENCE: 7

Leu Met Ala Thr Leu Lys Ala Pro Leu
 1               5

<210> SEQ ID NO 8
<211> LENGTH: 9
<212> TYPE: PRT
<213> ORGANISM: Artificial Sequence
<220> FEATURE:
<223> OTHER INFORMATION: Part of conformational epitope sequences of
```

```
            glycodelin monoclonal antibodies designated as
            8G8.3 and 3A10.25

<400> SEQUENCE: 8

Arg Trp Glu Asn Asn Ser Cys Val Glu
 1               5

<210> SEQ ID NO 9
<211> LENGTH: 9
<212> TYPE: PRT
<213> ORGANISM: Artificial Sequence
<220> FEATURE:
<223> OTHER INFORMATION: Part of conformational epitope sequences of
            glycodelin monoclonal antibodies designated as
            8G8.3 and 3A10.25

<400> SEQUENCE: 9

Lys Gln Met Glu Glu Pro Cys Arg Phe
 1               5
```

GLYCODELIN MONOCLONAL ANTIBODIES AND METHODS FOR THEIR USE IN THE DETECTION OF OVARIAN CANCER

CROSS-REFERENCE TO RELATED APPLICATIONS

This application claims the benefit of U.S. Provisional Application No. 61/158,159, filed Mar. 6, 2009, herein incorporated by reference in its entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 386096SEQLIST.txt, a creation date of Mar. 4, 2010, and a size of 6.45 KB. The sequence listing filed via EFS-Web is part of the specification and is hereby incorporated in its entirety by reference herein.

FIELD OF THE INVENTION

The invention relates to monoclonal antibodies capable of binding to glycodelin (also referred to in the art as "progestagen-associated endometrial protein" (PAEP)) and methods of using these antibodies, particularly in methods for diagnosing ovarian cancer and for identifying patients with an increased likelihood of having ovarian cancer. Hybridoma cell lines that produce these monoclonal antibodies are further disclosed.

BACKGROUND OF THE INVENTION

Ovarian cancer represents a heterogeneous group of diseases that affect women on a global basis. There are several forms of ovarian cancer which include epithelial cancer, germ-line cancer of the ovaries and ovarian stromal cancer. Epithelial ovarian cancer represents the most common form of the disease. Approximately 5-10% of epithelial ovarian cancer represents a hereditary form of the disease and three common patterns are recognized: ovarian cancer alone; ovarian and breast cancer linked to BRCA1 and BRCA2 genetic linkage on chromosomes 17q21 and 13q12 respectively; and ovarian and colon cancer. The most important risk factor for ovarian cancer is a first degree relative with the disease (e.g., a mother, sister or daughter with ovarian cancer). See, for example, Patridge et al. (1999) *CA-A Cancer Journal for Clinicians* 49:297-320. In 2005, there were an estimated 22,000 new cases of ovarian cancer diagnoses and 16,000 deaths from ovarian cancer. Ovarian cancer is the fifth leading cause of death of women and the leading cause of death from gynecological cancers. See generally American Cancer Society website at www.cancer.org; National Cancer Institute website cancer.gov available on the world wide web. Ovarian cancer is a disease that primarily affects post-menopausal women with the median age for diagnosis at 63 years of age. However, the disease can affect women of all age groups. See generally National Cancer Institute Surveillance, Epidemiology, and End Results (SEER) Program website seer.cancer.gov available on the world wide web.

The classification of ovarian cancer stage is based upon the extent of localization versus spread of the disease beyond the ovaries. Stage 1 ovarian cancer is confined to one or both of the ovaries. Stage 2 disease involves a tumor in one or both ovaries with pelvic extension. In Stage 3 ovarian cancer, a tumor is present in one or both ovaries with microscopically confirmed peritoneal metastasis outside the pelvis and/or regional lymph node metastasis. Stage 4 ovarian cancer is characterized by distant metastasis beyond the peritoneal cavity. Ovarian cancer is generally diagnosed in an advance stage of the disease due to the lack of specific clinical symptoms that would indicate the presence of small tumors. For women under the age of 50, less than 40% of ovarian cancers are detected when tumors are localized to one or both ovaries and when disease prognosis is best. For women over the age of 50, that number drops to less than 15%. Approximately 68% of women of all age groups afflicted with ovarian cancer are not diagnosed until distant metastasis is present. See generally National Cancer Institute Surveillance, Epidemiology, and End Results (SEER) Program website seer.cancer.gov available on the world wide web.

Ovarian cancer spreads via local shedding from the ovarian epithelium into the peritoneal cavity followed by implantation on the peritoneum and local invasion of the bowel and bladder. The presence of lymph node involvement in ovarian cancer is evident in all stages of diagnosed ovarian cancer. The percentage of positive lymph nodes increases significantly with progression of the disease (i.e., Stage 1, 24%; Stage 2, 50%, Stage 3, 74%; Stage 4, 73%). Id. The survival of patients with ovarian cancer is a function of the stage at which the disease is diagnosed, with the 5-year survival rate decreasing with advanced disease. More than 90% of women diagnosed with ovarian cancer in Stage 1 survive for at least 5 years following diagnosis. The 5-year survival rate drops to less than 30% when the disease is not diagnosed until Stage 4 (i.e., distant metastasis). Id.

Epithelial ovarian cancer is the most common form of the disease. There are four recognized major histological classes of epithelial ovarian cancer and these include serous, endometrioid, clear cell, and mucinous subtypes. The pathogenesis of ovarian cancer is poorly understood but it is believed to arise from ovarian surface epithelium. See Bell (2005) *Mod. Pathol.* 18 (Suppl. 2):519-32. Life factors that provide the greatest reduction in risk of ovarian cancer include multiparity, use of oral contraceptives, and breast feeding, all of which prevent ovulation. Because ovulation results in epithelial damage, followed by repair and possible inflammatory responses, repetition of this process throughout a woman's reproductive life without interruption appears to lead to cell damage and to increase the risk of ovarian cancer. See, for example, Ness et al. (1999) *J. Natl. Cancer Inst.* 91:1459-1467. However, there is no recognized, stepwise progression of ovarian cancer through defined precursor lesions, such as those recognized for both cervical carcinoma and colon cancer. Hence, considerable research has been directed at understanding the molecular basis for ovarian cancer and the basic differences between the various histological subtypes of ovarian cancer. Gene expression analyses have been utilized to provide this understanding and have identified a series of potential biomarkers for evaluation in diagnostic applications. See for example Ono et al. (2000) *Cancer Res.* 60:5007-11; Welsh et al. (2001) *Proc. Natl. Acad. Sci. USA* 98:1176-1181; Donninger et al. (2004) *Oncogene* 23:8065-8077; and Lee et al. (2004) *Int. J. Oncol.* 24(4): 847-851.

Ovarian cancer is often detected with the presentation of overt clinical symptoms, most notably the presentation of abdominal pain, an adnexal mass, abdominal bloating, and urinary urgency. As such, the detection of ovarian cancer is often detected at an advanced stage, where the prognosis and clinical outcome is poor. Detection of ovarian cancer at an early stage (i.e., Stage 1) results in an approximately 90% cure rate using standard surgery and chemotherapy; hence there is a clinical need to detect ovarian cancer at an early stage where treatment will be most effective. Unfortunately, current screening methods to detect early stage ovarian cancer are insufficient. The current practice for ovarian cancer screening employs the use of CA125 and transvaginal ultrasound (sonography). Rising serum levels of CA125 are sometimes associated with ovarian cancer and subsequent utilization of transvaginal ultrasound helps detect the presence of ovarian cancer. Confirmation of ovarian disease is based upon invasive procedures such as laparotomy.

CA125 serum testing is ineffective for general population screening due to issues of limited sensitivity, limited specificity, and a poor positive predictive value of <3%. Bast (2003) *J Clin Oncol.* 21(10 Suppl.):200-205. CA125 is a well characterized tumor marker normally expressed on the surface of epithelial cells and is generally detected in the serum of normal patients at 35 U/mL. Elevated serum levels of CA125 (>35 U/mL) are detected in approximately 85% of ovarian cancer patients. The remaining 15% of patients suffering from ovarian cancer, however, have normal serum levels of CA125. Furthermore, CA125 is elevated in only 50% of stage 1 ovarian cancer patients, thereby limiting its clinical utility in the early detection of ovarian cancer. As a result, there is no consensus on the recommendations for generally screening for ovarian cancer in the asymptomatic patient population. See National Cancer Institute website cancer.gov available on the world wide web. For high risk patients, the generally accepted procedures for the detection of ovarian cancer include the use of pelvic examinations, the use of CA125 serum testing, and transvaginal ultrasound (sonography). Patridge et al. (1999) *CA-A Cancer Journal for Clinicians* 49:297-320.

The low prevalence rates of ovarian cancer in the general population create additional challenges for the development of methods and screening tests that would promote early detection of the disease. Screening methods for diseases with low prevalence rates such as ovarian cancer often result in a high ratio of false positives to true positives, which limits the clinical utility of such screening programs. Given the significant risks associated with surgical exploration for possible ovarian cancer, a clinically useful screening test should refer to surgery no more than 10 women for every woman who actually has ovarian cancer (i.e., a positive predictive value (PPV) of at least 10%). Skates et al. (2004) *J. Clin. Oncol.* 22:4059-4066. PPV is highly dependent upon the prevalence rates for a particular disease or condition and will shift dramatically as a result of differences in disease prevalence. Therefore, with low-prevalence diseases, such as ovarian cancer, screening diagnostic tests with a relatively low PPV still have significant clinical utility. Potential ovarian cancer screening programs must be adjusted for the low prevalence of ovarian cancer and assessed for biomarker performance and clinical need. See, for example, Skates et al. (2004) *J. Clin. Oncol.* 22:4059-4066; Bast et al. (2005) *Int. J. Gynecol. Cancer* 15:274-281; and Rosen et al. (2005) *Gyn. Oncol.* 99:267-277. Despite efforts to identify a biomarker or panel of biomarkers for the detection, particularly early detection, of ovarian cancer, no adequate screening or diagnostic test that satisfies clinical needs currently exists. Currently available methods, such as detection of CA125, exhibit unacceptably high false-positive rates.

The current recommendations from the National Cancer Institute state that "there is insufficient evidence to establish that routine screening for ovarian cancer with serum markers such as CA125, transvaginal ultrasound or pelvic examinations would result in a decrease in mortality from ovarian cancer" (*NCI Summary of Evidence* (*Level 4, 5*); dated February 2005). In light of the serious risk of false-positives with currently available screening techniques, the NCI has not supported the institution of general screening procedures for ovarian cancer. As such, no standardized screening test exists for ovarian cancer, despite the fact that early diagnosis significantly improves 5-year survival rates.

As the 5-year survival rate for ovarian cancer depends greatly on the stage of the disease at the time of diagnosis, with increased survival associated with early detection (i.e., Stage 1 or 2), there is a need to identify more ovarian cancers at an earlier stage. The identification and characterization of biomarkers that permit earlier identification of ovarian cancers have the potential to improve the clinical outcome for many patients.

One candidate biomarker for ovarian cancer screening is glycodelin. Glycodelin is a member of the kernel lipocalin superfamily whose members share relatively low sequence similarity but have a highly conserved exon/intron structure and three-dimensional protein folding. Most lipocalins are clustered on the long arm of chromosome 9. The encoded glycoprotein has been previously referred to as pregnancy-associated endometrial alpha-2-globulin, placental protein 14, and glycodelin, but has been officially named progestagen-associated endometrial protein (PAEP). Three distinct forms, with identical protein backbones but different glycosylation profiles, are found in amniotic fluid, follicular fluid and seminal plasma of the reproductive system. These glycoproteins have distinct and essential roles in regulating a uterine environment suitable for pregnancy and in the timing and occurrence of the appropriate sequence of events in the fertilization process. A number of alternatively spliced transcript variants have been observed at this locus, but the full-length nature of only two, each encoding the same protein, has been determined. The literature landscape implicating glycodelin in ovarian cancer is fairly sparse but several publications have shown that glycodelin is useful as a prognostic indicator for ovarian cancer. See, for example, Kamarainen et al. (1996) *Am. J. Pathol.* 148:1435-1443; Song et al. (2001) *Proc. Nat'l Acad. Sci. USA* 98:9265-9270; Mandelin et al. (2003) *Cancer Research* 63:6258-6264; Jeschke et al. (2005) *Anticancer Research* 25:1581-1589), Jeschke et al. (2006) *Histopathology* 48:393-406; and Yurkovetsky et al. (2006) *Future Oncology* 2:733-741.

Therefore, a significant need exists in the art for reliable compositions (e.g., monoclonal antibodies) and methods that are capable of specifically identifying women that have ovarian cancer or an increased likelihood of having ovarian cancer. Women identified as having an increased likelihood of having ovarian cancer could be selected for more aggressive diagnostic methods to definitively determine if they presently have the disease. Moreover, such screening methods could be performed in the general female patient population on a routine basis to facilitate the detection of ovarian cancer in the earliest stages of the disease when prognosis and disease outcome are most favorable. Compositions and methods for monitoring efficacy of treatments and potential relapse of ovarian cancer are also needed.

SUMMARY OF THE INVENTION

Compositions and methods for detecting or diagnosing ovarian cancer in a patient or for identifying a patient with an increased likelihood of having ovarian cancer are provided. Compositions include monoclonal antibodies capable of binding to an ovarian cancer biomarker protein of interest, particularly glycodelin. Antigen-binding fragments and variants of the disclosed monoclonal antibodies, hybridoma cell lines capable of producing these antibodies, and kits comprising the monoclonal antibodies of the invention are also described herein.

The compositions of the invention find use in any method involving the detection of glycodelin, particularly methods for diagnosing ovarian cancer or identifying a patient with an increased likelihood of having ovarian cancer. The methods generally comprise detecting expression of at least one biomarker (e.g., glycodelin) in a patient body sample, wherein overexpression of the biomarker or a plurality of biomarkers is indicative of ovarian cancer or an increased likelihood of the patient having ovarian cancer. In particular, the methods comprise using one or more of the antibodies of the invention to detect expression of glycodelin in a patient body sample. Methods for assessing the efficacy of a particular therapy for ovarian cancer in a patient and for monitoring the regression or progression of ovarian cancer in a patient are also disclosed herein.

The methods for diagnosing ovarian cancer in a patient or identifying a patient with an increased likelihood of having ovarian cancer may comprise, for example, detecting overexpression of glycodelin protein in a patient body sample via a two-antibody or "sandwich" ELISA (enzyme-linked immunosorbent assay) technique, as described herein. Such screening methods generally comprise detecting in a patient body sample expression of one or a plurality of biomarkers that are selectively overexpressed in ovarian cancer. Overexpression of the one or more biomarkers is indicative of an increased likelihood that the patient has ovarian cancer.

The methods of the invention may comprise, for example, a "two-step" analysis, wherein a first assay step is performed to detect the expression of a first biomarker (e.g., glycodelin) or a panel of biomarkers. If the first biomarker or panel of biomarkers is overexpressed, a second assay step is performed to detect the expression of a second biomarker or panel of biomarkers. Overexpression of the first and second biomarkers or panels of biomarkers is indicative of an increased likelihood that the patient has ovarian cancer. The methods of the invention may utilize the disclosed glycodelin antibodies to detect expression of glycodelin in a patient sample. The compositions and methods of the invention may be further utilized in the diagnosis or detection of other types of cancer.

Compositions of the invention further include isolated polypeptides that comprise an epitope capable of binding a glycodelin monoclonal antibody of the invention. These polypeptides find use in methods for producing glycodelin antibodies. Isolated nucleic acid molecules encoding the amino acid sequences of the glycodelin epitopes are also provided.

BRIEF DESCRIPTION OF THE DRAWINGS

FIG. 1 provides the results of analyses that were performed to identify preferred complementary pairings of the glycodelin monoclonal antibodies of the invention for use in sandwich ELISA immunoassays. Specifically, the 2G7.1 glycodelin antibody was bound to a solid support and used as the capture antibody and tested in conjunction with various labeled glycodelin monoclonal detector antibodies (e.g., the 8G8.3 and 3A10.25 glycodelin antibodies).

DETAILED DESCRIPTION OF THE INVENTION

Figure 1A:
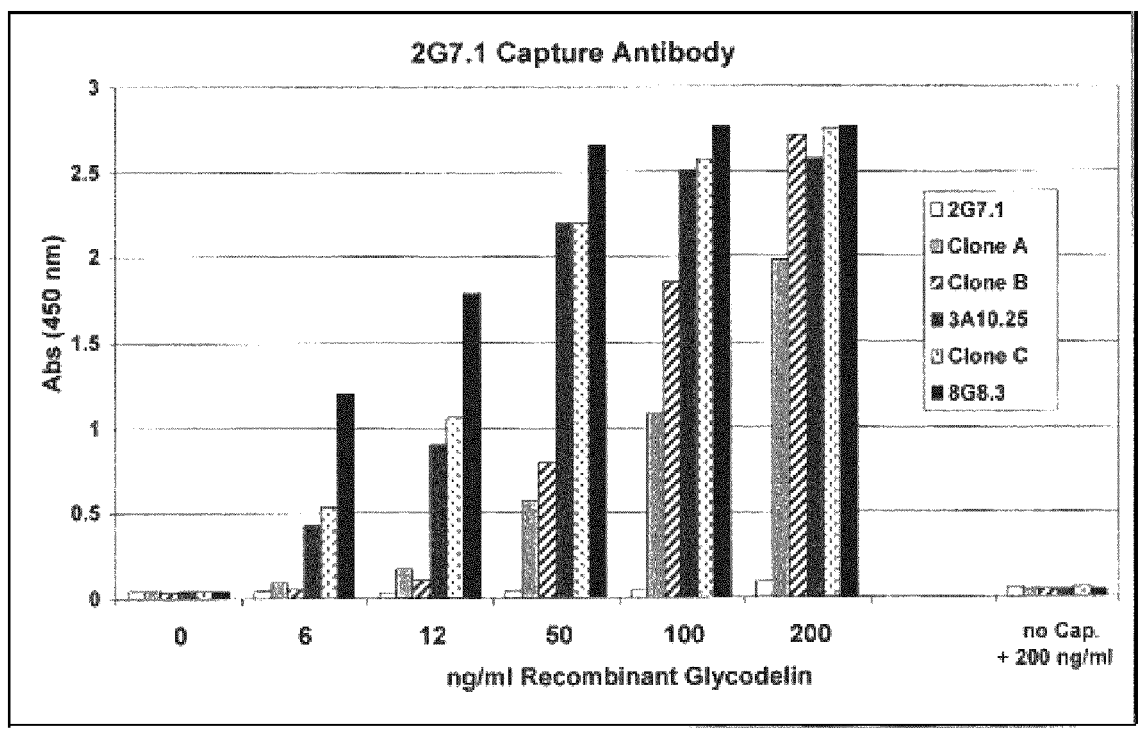
FIG. 1A provides the results achieved with increasing concentrations of recombinant glycodelin as the "target" antigen.

Compositions and methods for diagnosing ovarian cancer or identifying a patient having an increased likelihood of having ovarian cancer are provided. Compositions include monoclonal antibodies that are capable of binding to the biomarker protein glycodelin, which is selectively overexpressed in ovarian cancer. By "selectively overexpressed in ovarian cancer" is intended that the biomarker of interest is overexpressed in ovarian cancer but is not overexpressed in conditions classified as nonmalignant, benign, and other conditions that are not considered to be clinical disease. Hybridoma cell lines that produce the monoclonal antibodies of the present invention are also disclosed. Kits comprising the monoclonal antibodies described herein are further provided.

The compositions of the invention include monoclonal antibodies that specifically bind to glycodelin, or to a variant or fragment thereof. The amino acid and nucleotide sequences for glycodelin are set forth in SEQ ID NO:1 (Accession No. NP_001018059.1) and SEQ ID NO:2 (Accession No. NM_001018049), respectively. In particular embodiments, the glycodelin monoclonal antibodies designated as 2G7.1, 8G8.3, and 3A10.25 are provided. A hybridoma cell line that produces glycodelin monoclonal antibody 2G7.1 was deposited with the Patent Depository of the American Type Culture Collection (ATCC), Manassas, Va., 20110-2209 on Jan. 7, 2009 and assigned Patent Deposit No. PTA-9684. A hybridoma cell line that produces glycodelin monoclonal antibody 8G8.3 was deposited with the Patent Depository of the American Type Culture Collection (ATCC), Manassas, Va., 20110-2209 on Jan. 7, 2009 and assigned Patent Deposit No. PTA-9685. A hybridoma cell line that produces glycodelin monoclonal antibody 3A10.25 was deposited with the Patent Depository of the American Type Culture Collection (ATCC), Manassas, Va., 20110-2209 on Jan. 7, 2009 and assigned Patent Deposit No. PTA-9686. These deposits will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. §1.808, sample(s) of the deposits with the ATCC and restrictions on the accessibility of the deposits will be irrevocably withdrawn by the Applicants. These deposits will be replaced if viable samples cannot be dispensed by the ATCC. This deposit was made merely as a convenience for those of skill in the art and are not an admission that a deposit is required under 35 U.S.C. §112.

Antibodies that have the binding characteristics of monoclonal antibodies 2G7.1, 8G8.3, and 3A10.25 are also disclosed herein. Such antibodies include, but are not limited to, antibodies that compete in competitive binding assays with these antibodies, as well as antibodies that bind to an epitope capable of binding glycodelin monoclonal antibody 2G7.1, 8G8.3, or 3A10.25. Methods for assessing whether antibodies have the same or similar binding characteristics include traditional quantitative methods such as, for example, determining and comparing antibody affinity or avidity for the antigen (e.g., glycodelin). See, for example, Roitt et al., eds. (1989) *Immunology* (Glower Medical Publishing, London)

and Kuby (1992) *Immunology* (W.H. Freeman and Company, New York). Other exemplary methods for comparing the binding characteristics of antibodies include western blotting, enzyme immunoassays, ELISA, and flow cytometry. Methods for assessing and comparing antibody-antigen binding characteristics are well known in the art. Variants and fragments of monoclonal antibodies 2G7.1, 8G8.3, and 3A10.25 that retain the ability to specifically bind to glycodelin are also provided. Compositions further include hybridoma cell lines that produce the monoclonal antibodies of the present invention and kits comprising at least one monoclonal antibody disclosed herein.

"Antibodies" and "immunoglobulins" (Igs) are glycoproteins having the same structural characteristics. While antibodies exhibit binding specificity to an antigen, immunoglobulins include both antibodies and other antibody-like molecules that lack antigen specificity. Polypeptides of the latter kind are, for example, produced at low levels by the lymph system and at increased levels by myelomas.

The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site. Antibody derivatives may comprise a protein or chemical moiety conjugated to the antibody. The term "antibody" is used in the broadest sense and covers fully assembled antibodies, antibody fragments that can bind antigen (e.g., Fab', F'(ab)$_2$, Fv, single chain antibodies, diabodies), and recombinant peptides comprising the foregoing. As used herein, "glycodelin antibody" refers to any antibody that specifically binds to glycodelin (SEQ ID NO:1), or to a variant or fragment thereof, and includes monoclonal antibodies, polyclonal antibodies, single-chain antibodies, and fragments thereof which retain the antigen binding function of the parent antibody.

The glycodelin antibodies of the invention are optimally monoclonal antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (V,) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity determining regions (CDRs) or hypervariable regions both in the light chain and the heavy-chain variable domains. The more highly conserved portions of variable domains are called the framework (FR) regions. The variable domains of native heavy and light chains each comprise four FR regions, largely adopting a p-sheet configuration, connected by three CDRs, which form loops connecting, and in some cases forming part of, the p-sheet structure. The CDRs in each chain are held together in close proximity by the FR regions and, with the CDRs from the other chain, contribute to the formation of the antigen-binding site of antibodies (see Kabat et al., NIH Publ. No. 91-3242, Vol. I, pages 647-669 (1991)).

The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarily determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institute of Health, 25 Bethesda, Md. [1991]) and/or those residues from a "hypervariable loop" (i.e., residues 26-32 (L1), 50-52 (L2) and 91-96 (L3) in the light chain variable domain and 26-32(H1), 53-55 (H2) and 96-101 (H3) in the heavy chain variable domain; Clothia and Lesk, J. Mol. Biol., 196:901-917 [1987]). Framework" or "FR" residues are those variable domain residues other than the hypervariable region residues as herein deemed.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) *Protein Eng.* 8(10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment of antibodies yields an F(ab')2 fragment that has two antigen-combining sites and is still capable of cross-linking antigen.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them.

Fragments of the claimed glycodelin monoclonal antibodies are encompassed by the invention so long as they retain the desired function of the full-length antibody (i.e., the ability to selectively bind to glycodelin). Thus, for example, a fragment of a glycodelin monoclonal antibody of the invention will retain the ability to bind to a glycodelin antigen. Such fragments are characterized by properties similar to the corresponding full-length antibody, that is, the fragments will specifically bind glycodelin. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, F(ab')$_2$, and Fv fragments and single-chain antibody molecules. By "Fab" is intended a monovalent antigen-binding fragment of an immunoglobulin that is composed of the light chain and part of the heavy chain. By "F(ab')$_2$" is intended a bivalent antigen-binding fragment of an immunoglobulin that contains both light chains and part of both heavy chains. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the $V_H$ and $V_L$ domains that enables the sFv to form the desired structure for antigen binding. For a review of sFv see Pluckthun (1994) in *The Pharmacology of Monoclonal Antibodies*, Vol. 113, ed. Rosenburg and Moore (Springer-Verlag, New York), pp. 269-315.

Antibodies or antibody fragments can be isolated from antibody phage libraries generated using the techniques described in, for example, McCafferty et al. (1990) *Nature* 348:552-554 (1990) and U.S. Pat. No. 5,514,548. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. (1992) *Bio/Technology* 10:163-167). According to another approach, F(ab')$_2$ fragments can be isolated directly from recombinant host cell culture. Other techniques for the production of antibody fragments will be apparent to the skilled practitioner.

In some embodiments, antibodies of the invention are monoclonal in nature. As indicated above, "monoclonal antibody" is intended an antibody obtained from a population of substantially homogeneous antibodies, i.e., the individual antibodies comprising the population are identical except for possible naturally occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site, i.e., a particular epitope within the glycodelin protein, as defined herein below. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in, for example, Clackson et al. (1991) *Nature* 352:624-628; Marks et al. (1991) *J. Mol. Biol.* 222:581-597; and U.S. Pat. No. 5,514,548.

Monoclonal antibodies can be prepared using the method of Kohler et al. (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen (i.e., antibody-producing cells) bind to the plate and are not rinsed away. Resulting B cells, or all dissociated spleen cells, are then induced to fuse with myeloma cells to form monoclonal antibody-producing hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice). Monoclonal antibodies can also be produced using Repetitive Immunizations Multiple Sites technology (RIMMS). See, for example, Kilpatrick et al. (1997) *Hybridoma* 16(4):381-389; Wring et al. (1999) *J. Pharm. Biomed. Anal.* 19(5):695-707; and Bynum et al. (1999) *Hybridoma* 18(5):407-411, all of which are herein incorporated by reference in their entirety.

As an alternative to the use of hybridomas, antibody can be produced in a cell line such as a CHO cell line, as disclosed in U.S. Pat. Nos. 5,545,403; 5,545,405; and 5,998,144; incorporated herein by reference. Briefly, the cell line is transfected with vectors capable of expressing a light chain and a heavy chain, respectively. By transfecting the two proteins on separate vectors, chimeric antibodies can be produced. Another advantage is the correct glycosylation of the antibody. A monoclonal antibody can also be identified and isolated by screening a recombinant combinatorial immunoglobulin library (e.g., an antibody phage display library) with a biomarker protein to thereby isolate immunoglobulin library members that bind the biomarker protein. Kits for generating and screening phage display libraries are commercially available (e.g., the Pharmacia *Recombinant Phage Antibody System*, Catalog No. 27-9400-01; and the Stratagene *SurfZAP θ Phage Display Kit*, Catalog No. 240612). Additionally, examples of methods and reagents particularly amenable for use in generating and screening an antibody display library can be found in, for example, U.S. Pat. No. 5,223,409; PCT Publication Nos. WO 92/18619; WO 91/17271; WO 92/20791; WO 92/15679; 93/01288; WO 92/01047; WO 92/09690; and WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734. The methods utilized in the production of glycodelin monoclonal antibodies 2G7.1, 8G8.3, and 3A10.25 are set forth in Example 1 below.

In some aspects of the invention, antibodies may be selected on the basis of desirable staining of cytological or histological samples. That is, in particular embodiments the antibodies are selected with the end sample type (e.g., cytology preparations; tissue samples) in mind and for binding specificity. Antibodies directed to glycodelin are selected and purified via a multi-step screening process. Such methods for antibody selection are described in U.S. Pat. No. 7,157,233, which is herein incorporated by reference in its entirety. Moreover, particular glycodelin antibody pairings or larger groupings may be chosen for use in a certain assay format for optimal results (e.g., sandwich ELISA, etc).

Antibodies having the binding characteristics of a monoclonal antibody of the invention are also provided. "Binding characteristics" or "binding specificity" when used in reference to an antibody means that the antibody recognizes the same or similar antigenic epitope as a comparison antibody. Examples of such antibodies include, for example, an antibody that competes with a monoclonal antibody of the invention in a competitive binding assay. One of skill in the art could determine whether an antibody competitively interferes with another antibody using standard methods.

By "epitope" is intended the part of an antigenic molecule to which an antibody is produced and to which the antibody will bind. A "glycodelin epitope" comprises the part of the glycodelin protein to which a glycodelin monoclonal antibody binds. Epitopes can comprise linear amino acid residues (i.e., residues within the epitope are arranged sequentially one after another in a linear fashion), nonlinear amino acid residues (referred to herein as "nonlinear epitopes" or "conformational epitopes"; these epitopes are not arranged sequentially), or both linear and nonlinear amino acid residues. Nonlinear epitopes or conformational epitopes can also include amino acid residues that contribute to the overall conformation of the recognition structure of the antibody, but do not necessarily bind the antibody. Typically, epitopes are short amino acid sequences, e.g. about five amino acids in length. Systematic techniques for identifying epitopes are known in the art and are described, for example, in U.S. Pat. No. 4,708,871 and in the examples set forth below. Briefly, in one method, a set of overlapping oligopeptides derived from the antigen may be synthesized and bound to a solid phase array of pins, with a unique oligopeptide on each pin. The array of pins may comprise a 96-well microtiter plate, permitting one to assay all 96 oligopeptides simultaneously, e.g., for binding to a biomarker-specific monoclonal antibody. Alternatively, phage display peptide library kits (New England BioLabs) are currently commercially available for epitope mapping. Using these methods, the binding affinity for every possible subset of consecutive amino acids may be determined in order to identify the epitope that a given antibody binds. Epitopes may also be identified by inference when epitope length peptide sequences are used to immunize animals from which antibodies are obtained. Conformational epitopes may be identified using peptide walking techniques and synthetic peptides (see, for example, Liang et al. (2005) *Clinical Chemistry* 51:1382-1396; Cochran et al. (2004) *J. Immunol. Meth.* 287:147-158; Teeling et al. (2006) *J. Immunol.* 177:362-371; Timmerman et al. (2004) *Molecular Diversity* 8:61-77; Lekcharoensuk et al. (2004) *J. Virology* 78:8135-8145; and Casadio et al. (2007) *BMC Bioinformatics* (Supp. 1):S1-6; each of which is herein incorporated by reference in its entirety), such as CLIPS™ (chemically-linked immunogenic peptides on scaffolds) technology, available from Pepscan Presto (see, for example, Timmerman et al. (2009) *Open Vaccine J* 2:56-67; Meloen et al. (1997) Epitope mapping by PEPSCAN. In: Immunology Methods Manual, Ed. Iwan Lefkovits, Academic Press, pp 982-988; and the Pepscan Presto website available on the world wide web at pepscanpresto.com; each of which is herein incorporated by reference in its entirety).

The invention provides antibodies that recognize the same epitope as monoclonal antibody 2G7.1, 8G8.3, or 3A10.25. The antibody can recognize the epitope sequence set forth in SEQ ID NO:3 or 5, which are recognized by the 2G7.1 antibody. In some embodiments, the epitope sequence comprises SEQ ID NO:5 in addition to at least one of SEQ ID NO: 6 and 7. In these embodiments, the epitope sequence comprises SEQ ID NO:5 at the amino acid residue positions corresponding to positions 131 through 134 of SEQ ID NO:1, and can further comprise at least one of SEQ ID NO:6 at the amino acid residue positions corresponding to positions 159 through 162 of SEQ ID NO:1, and SEQ ID NO:7 at the amino acid residue positions corresponding to positions 49 through 57 of SEQ ID NO:1.

Antibodies that recognize the epitope of monoclonal antibody 8G8.3 or 3A10.25 are also provided. In these embodiments, the epitope sequence can comprise at least one of (and in some embodiments, all of) SEQ ID NO:5, 6, 7, 8, and 9. In some of these embodiments, the epitope comprises at least one of (and in some embodiments, all of) the following sequences: SEQ ID NO:7 at the amino acid residue positions corresponding to positions 49 through 57 of SEQ ID NO:1, SEQ ID NO:8 at the amino acid residue positions corresponding to positions 78 through 86 of SEQ ID NO:1, SEQ ID NO:5 at the amino acid residue positions corresponding to positions 131 through 134 of SEQ ID NO:1, SEQ ID NO:6 at the amino acid residue positions corresponding to positions 159 through 162 of SEQ ID NO:1, and SEQ ID NO:9 at the amino acid residue positions corresponding to positions 172 through 180 of SEQ ID NO:1.

As used herein, an amino acid residue of an epitope at the position corresponding to a particular amino acid residue of a glycodelin sequence (e.g., SEQ ID NO:1) refers to the amino acid residue within the epitope that appears opposite the amino acid residue at a particular position in the glycodelin sequence when the epitope sequence is aligned with the glycodelin sequence (e.g., SEQ ID NO:1) for maximum homology using an alignment program, such as one known in the art (e.g., the GAP program in the GCG software package, using either a BLOSUM62 matrix or a PAM250 matrix).

The invention also encompasses isolated polypeptides comprising an epitope for binding a glycodelin monoclonal antibody of the invention. These polypeptides correspond to a portion of the glycodelin antigen that binds to monoclonal antibody 2G7.1, 8G8.3, or 3A10.25. Such polypeptides find use in methods for producing antibodies that selectively bind to glycodelin. The ability of a polypeptide to be used in the production of antibodies is referred to herein as "antigenic activity." For example, the amino acid sequence set forth in SEQ ID NO:5 (corresponding to residues 131 through 134 in the glycodelin amino acid sequence set forth in SEQ ID NO:1) comprises the minimal epitope recognized by a glycodelin monoclonal antibody, more particularly monoclonal antibody 2G7.1. The amino acid sequence set forth in SEQ ID NO:3 (corresponding to residues 110 to 140 in the glycodelin amino acid sequence set forth in SEQ ID NO:1) comprises a larger immunogenic region of glycodelin that is recognized by monoclonal antibody 2G7.1. Further, in some embodiments, the isolated polypeptide comprises an epitope for binding a glycodelin monoclonal antibody that comprises SEQ ID NO:5 in addition to at least one of SEQ ID NO: 6 and 7. In these embodiments, the epitope sequence comprises SEQ ID NO:5 at the amino acid residue positions corresponding to positions 131 through 134 of SEQ ID NO:1, and can further comprise at least one of SEQ ID NO:6 at the amino acid residue positions corresponding to positions 159 through 162 of SEQ ID NO:1, and SEQ ID NO:7 at the amino acid residue positions corresponding to positions 49 through 57 of SEQ ID NO:1. In other embodiments, the isolated polypeptide comprises an epitope for binding a glycodelin monoclonal antibody that comprises at least one of (and in some embodiments, all of) SEQ ID NO:5, 6, 7, 8, and 9. In some of these embodiments, the epitope comprises at least one of (and in some embodiments, all of) the following sequences: SEQ ID NO:7 at the amino acid residue positions corresponding to positions 49 through 57 of SEQ ID NO:1, SEQ ID NO:8 at the amino acid residue positions corresponding to positions 78 through 86 of SEQ ID NO:1, SEQ ID NO:5 at the amino acid residue positions corresponding to positions 131 through 134 of SEQ ID NO:1, SEQ ID NO:6 at the amino acid residue positions corresponding to positions 159 through 162 of SEQ ID NO:1, and SEQ ID NO:9 at the amino acid residue positions corresponding to positions 172 through 180 of SEQ ID NO:1

Variants and fragments of the sequences set forth in SEQ ID NO:3, 5, 6, 7, 8, and 9 and combinations thereof that retain the antigenic activity of the original polypeptide are also provided. The invention further includes isolated nucleic acid molecules that encode the polypeptide that comprises the epitope sequence set forth in SEQ ID NO:3, 5, 6, 7, 8 or 9, or combinations thereof, and variants and fragments thereof.

The polypeptide of the invention comprising a glycodelin epitope can be used in methods for producing monoclonal antibodies that specifically bind to glycodelin, as described herein above. Such a polypeptide can also be used in the production of polyclonal glycodelin antibodies. For example, polyclonal antibodies can be prepared by immunizing a suitable subject (e.g., rabbit, goat, mouse, or other mammal) with a polypeptide comprising a glycodelin epitope (i.e., an immunogen). The antibody titer in the immunized subject can be monitored over time by standard techniques, such as with an ELISA using an immobilized biomarker protein (e.g., glycodelin). At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (Kozbor et al. (1983) Immunol. Today 4:72), the EBV-hybridoma technique (Cole et al. (1985) in Monoclonal Antibodies and Cancer Therapy, ed. Reisfeld and Sell (Alan R. Liss, Inc., New York, N.Y.), pp. 77-96) or trioma techniques. The technology for producing hybridomas is well known (see generally Coligan et al., eds. (1994) Current Protocols in Immunology (John Wiley & Sons, Inc., New York, N.Y.); Galfre et al. (1977) Nature 266:550-52; Kenneth (1980) in Monoclonal Antibodies: A New Dimension In Biological Analyses (Plenum Publishing Corp., NY; and Lerner (1981) Yale J. Biol. Med., 54:387-402).

Amino acid sequence variants of a monoclonal antibody or a polypeptide comprising a glycodelin epitope described herein are also encompassed by the present invention. Variants can be prepared by mutations in the cloned DNA sequence encoding the antibody or polypeptide of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) Proc. Natl. Acad. Sci. USA 82:488-492; Kunkel et al. (1987) Methods Enzymol. 154:367-382; Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the polypeptide of interest, modifications are made such that variants continue to possess the desired activity, i.e., similar binding affinity to the biomarker. Obviously, any mutations made in the DNA encoding the variant polypeptide must not place the sequence out of reading frame and preferably will not create complementary regions that could produce secondary mRNA structure. See EP Patent Application Publication No. 75,444.

The variants of a reference polypeptide generally have amino acid sequences that have at least 70% or 75% sequence identity, particularly at least 80% or 85% sequence identity, more particularly at least 90%, 91%, 92%, 93%, 94% or 95% sequence identity to the amino acid sequence for the reference antibody molecule, or to a shorter portion of the reference antibody molecule. Optimally, the molecules share at least 96%, 97%, 98%, 99%, or more sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant may, for example, differ from the reference antibody by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more contiguous amino acid residues. Corrections for sequence identity associated with conservative residue substitutions or gaps can be made (see Smith-Waterman homology search algorithm).

The glycodelin monoclonal antibodies of the invention may be labeled with a detectable substance as described below to facilitate glycodelin biomarker protein detection in a sample. Such antibodies find use in practicing the methods of the invention. The antibodies and antibody fragments of the invention can be coupled to a detectable substance to facilitate detection of antibody binding. The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Examples of detectable substances for purposes of labeling antibodies include various enzymes, prosthetic groups, fluorescent materials, luminescent materials, bioluminescent materials, and radioactive materials. Examples of suitable enzymes include but are not limited to horseradish peroxidase, alkaline phosphatase, β-galactosidase, or acetylcholinesterase; examples of suitable prosthetic group complexes include but are not limited to streptavidin/biotin and avidin/biotin; examples of suitable fluorescent materials include but are not limited to umbelliferone, fluorescein, fluorescein isothiocyanate, rhodamine, dichlorotriazinylamine fluorescein, dansyl chloride or phycoerythrin; an example of a luminescent material includes but is not limited to luminol; examples of bioluminescent materials include but are not limited to luciferase, luciferin, and aequorin; and examples of suitable radioactive material include $^{125}$I, $^{131}$I, $^{35}$S, or $^{3}$H. Other exemplary detectable labels for use in the practice of the instant invention include digoxigenin and quantum dots.

Although the glycodelin monoclonal antibodies disclosed herein may be used in any method in which detection of glycodelin protein is desirable, the glycodelin monoclonal antibody compositions of the invention find particular use in methods for detecting or diagnosing ovarian cancer or identifying patients with an increased likelihood of having ovarian cancer, such as by the methods disclosed in U.S. Patent Application Publication No. 2007/0212721, which is herein incorporated by reference in its entirety. By "ovarian cancer" is intended those conditions classified by post-exploratory laparotomy as premalignant pathology, malignant pathology, and cancer (FIGO Stages 1-4). Staging and classification of ovarian cancer are described in detail above. "Early-stage ovarian cancer" refers to those disease states classified as Stage 1 or Stage 2 carcinoma. Early detection of ovarian cancer significantly increases 5-year survival rates. As used herein, "identifying patients with an increased likelihood of having ovarian cancer" is intended methods for classifying those females that are more likely to have ovarian cancer so that additional tests and monitoring can be performed, particularly to detect ovarian cancer at an early stage during which prognosis is most favorable. An "increased likelihood of having ovarian cancer" is intended to mean that patients who are determined in accordance with the present methods to exhibit overexpression of particular biomarkers are more likely to have ovarian cancer than those patients who do not.

As used herein, "patient" or "subject" is intended an animal, including a mammal, particularly a human. The patient or subject may or may not be suspected of having ovarian cancer (e.g., exhibiting symptoms, tested positive for another ovarian cancer biomarker).

"Diagnosing ovarian cancer" is intended to include, for example, diagnosing or detecting the presence of ovarian cancer, monitoring the progression of the disease, and identifying or detecting cells or samples that are indicative of ovarian cancer. The terms diagnosing, detecting, and identifying ovarian cancer are used interchangeably herein. Although the methods of the invention can identify patients more likely to have to ovarian cancer and to aid in the diagnosis of this disease, particularly at an early stage, a "definitive" diagnosis of ovarian cancer will generally comprise performing a biopsy on a tissue sample from the subset of patients identified by the methods of the invention.

The term "screening method" refers to strategies to identify patients that have an increased likelihood of having ovarian cancer so that such patients can be selected for more aggressive diagnostic methods to definitively determine if the patients have ovarian cancer. The "screening methods" of the invention are generally not intended to definitively diagnose a patient as having (or not having) ovarian cancer. Rather, such methods are intended to identify women having an increased likelihood of having ovarian cancer so that these women may undergo additional diagnostic methods to obtain a definitive diagnosis. That is, a patient that is identified as having ovarian cancer or an increased likelihood of having ovarian cancer in accordance with the disclosed methods may be subjected to further diagnostic testing to definitively determine if the patient has ovarian cancer. "Further diagnostic testing" includes but is not limited to pelvic examination, transvaginal ultrasound, CT scan, MRI, laparotomy, laparoscopy, and biopsy. Such diagnostic methods are well known in the art. Moreover, patients classified as having an increased likelihood of having ovarian cancer that are determined by further diagnostic testing not to currently have ovarian cancer may be closely monitored on a regular basis for the development of ovarian cancer. Monitoring of such patients may include but is not limited to periodic pelvic examination, transvaginal ultrasound, CT scan, and MRI. A physician of ordinary skill in the art will appreciate appropriate techniques for monitoring patients for the development of ovarian cancer. The screening methods of the invention may be performed on a case-by-case basis or as a periodic routine screening test for the general female population. In some embodiments, the screening methods for identifying patients with an increased likelihood of having ovarian cancer may be viewed as comparable to Pap smears for the identification of patients having an increased likelihood of having cervical cancer.

In another embodiment of the invention, a two antibody or ELISA format is used to diagnose ovarian cancer or to identify a patient with an increased likelihood of having ovarian cancer by detecting overexpression of glycodelin in a patient body sample. Such sandwich or "two-site" immunoassays are known in the art. See, for example, Current Protocols in Immunology. *Indirect Antibody Sandwich ELISA to Detect Soluble Antigens*, John Wiley & Sons, 1991. In the certain sandwich ELISA methods encompassed by the invention, two antibodies specific to two distinct antigenic sites on glycodelin are used, such as, for example, the glycodelin monoclonal antibodies designated as 2G7.1, 8G8.3, and 3A10.25. By "distinct antigenic site" is intended that the antibodies are specific for different sites on the biomarker protein of interest (i.e., glycodelin) such that binding of one antibody does not significantly interfere with binding of the other antibody to the biomarker protein. Sandwich ELISA techniques utilize two antibodies: a "capture" antibody and a "detector" antibody. The first antibody, the "capture antibody," is generally immobilized on or bound to a solid support. For example, a capture antibody may be covalently or noncovalently attached to a cell culture plate, microtiter cell culture plate well, a bead (e.g., MAGPLEX® magnetic microbeads), a cuvette, nanoparticle, or other reaction vessel. In certain aspects of the invention, the capture antibody is bound to a microtiter plate well. Methods for attaching an antibody to a solid support are routine in the art. The patient body sample, particularly a blood sample, more particularly a serum sample, is then contacted with the capture antibody-bound solid support and allowed to form a complex with the capture antibody. Unbound sample is removed, and a second antibody, the "detector" or "tag" antibody, is exposed to the solid support containing the capture antibody-antigen complex. The detector antibody is specific for a distinct antigenic site on the biomarker of interest (e.g., glycodelin) and is coupled to or labeled with a detectable substance, as described herein. Such antibody labels are well known in the art and include various enzymes, prosthetic groups, fluorescent materials (e.g., enzymes (e.g., horseradish peroxidase (HRP)), phycoerythrin, luminescent materials, bioluminescent materials, and radioactive materials). Following incubation with the detector antibody, unbound sample is removed, and glycodelin expression levels are determined by quantitating the level of labeled detector antibody bound to the solid support, which in turn directly correlates with the level of glycodelin present in the sample. This quantitation step can be performed by a number of known techniques and will vary depending on the specific detectable substance coupled to the detector antibody, as would be appreciated by those of skill in the art.

The methods of the invention generally comprise detecting overexpression of at least one biomarker, more particularly a plurality of biomarkers, that is selectively overexpressed in ovarian cancer in a patient body sample. Thus, detection of the biomarkers permits the differentiation of samples indicative of an increased likelihood of having ovarian cancer or the presence of ovarian cancer from normal samples (i.e., samples from patients that are ovarian-cancer free) and samples that are indicative of nonmalignant and benign proliferation. A biomarker of particular interest in the detection, diagnosis, or monitoring of ovarian cancer is glycodelin. One of skill in the art will appreciate that in addition to the detection of glycodelin expression, the methods of the invention for detecting ovarian cancer and for identifying a patient with an increased likelihood of having ovarian cancer further encompass the detection of a plurality of biomarkers that are selectively expressed in ovarian cancer. For example, other biomarkers of interest, include but are not limited to HE4, CA125, MMP-7, Muc-1, PAI-1, CTHRC1, inhibin, PLAU-R, prolactin, KLK-10, KLK-6, and SLPI, alpha-1 anti-trypsin (AAT), Imp-2, FLJ10546, FLJ23499, MGC13057, SPON1, S100A1, SLC39A4, TACSTD2, MBG2, HETKL27 (MAL2), Cox-1, protein kinase C-iota, cadherin-6, ADPRT, matriptase, folate receptor, claudin 4, mesothelin, aquaporin 5, cofilin 1, gelsolin, clusterin, alpha tetranectin, vitronectin, pregnancy-associated plasma protein-A (PAPP-A), folistatin, B7-H4, YKL-40, claudin 3, elafin, and KOP. Biomarkers of particular interest include HE4, CA125, glycodelin, Muc-1, PAI-1, CTHRC1, inhibin, PLAU-R, prolactin, KLK-10, KLK-6, SLPI, and alpha-1 anti-trypsin. Antibodies for the detection of these exemplary ovarian cancer biomarkers are known in the art or can be produced in accordance with routine methods.

As used herein, "body sample" refers to any sampling of cells, tissues, or bodily fluids from a patient in which expression of a biomarker can be detected. Examples of such body samples include but are not limited to blood (e.g., whole blood, blood serum, blood having platelets removed, etc.), lymph, ascitic fluids, urine, gynecological fluids (e.g., ovarian, fallopian, uterine secretion, menses, etc.), biopsies, and fluids obtained during laparoscopy. Body samples may be obtained from a patient by a variety of techniques including, for example, by venipuncture, by scraping or swabbing an area, or by using a needle to aspirate bodily fluids or tissues. Methods for collecting various body samples are well known in the art. In particular embodiments, the body sample comprises blood or serum.

In a particular aspect of the invention, the methods comprise obtaining a sample (e.g., blood or serum) from a patient, contacting the sample with at least one glycodelin monoclonal antibody of the invention, and detecting binding of the antibody to the glycodelin protein. In other embodiments, the sample is contacted with at least two monoclonal antibodies that bind to glycodelin. Techniques for detecting antigen (e.g., glycodelin)-antibody binding are well known in the art. Antibody binding to a biomarker of interest may be detected, for example, through the use of chemical reagents that generate a detectable signal that corresponds to the level of antibody binding and, accordingly, to the level of biomarker protein expression. Any method for detecting antibody-antigen (e.g., glycodelin) binding may be used to practice the methods of the invention. Such methods include but are not limited to traditional enzyme immunoassays (EIA), sandwich ELISA techniques (as described herein below), western blotting, immunocytochemistry, immunohistochemistry, immunoprecipitation, flow cytometry, Raman spectroscopy of nanoparticles, multiplex bead-based assays (e.g., using MAGPLEX® magnetic beads and a fluorescent tag such as phycoerythrin or utilizing the LUMINEX® platform).

The methods of the invention for diagnosing ovarian cancer in a patient or for identifying patients with an increased likelihood of having ovarian cancer, such as the sandwich ELISA, may further comprise comparing the level of glycodelin protein in a patient body sample to a threshold level to determine if the patient has ovarian cancer or has an increased likelihood of having ovarian cancer. As used herein, "threshold level" refers to a level of glycodelin expression above which a patient sample is deemed "positive" and below which the sample is classified as "negative" for ovarian cancer or an increased likelihood of having ovarian cancer. A threshold expression level for a particular biomarker (e.g., glycodelin) may be based on one or more compilations of data from "normal" patient samples (i.e., a patient population of females who do not have ovarian cancer). For example, the threshold expression level may be established as the value within two standard deviations of the mean glycodelin expression level, based on the analysis of "normal" samples from patients who do not have ovarian cancer. One of skill in the art will appreciate that a variety of statistical and mathematical methods for establishing the threshold level of expression are known in the art.

The skilled artisan in the art would further recognize that the capture and detector antibodies can be contacted with the body sample sequentially, as described above, or simultaneously. Furthermore, the detector antibody can be incubated with the body sample first, prior to contacting the sample with the immobilized capture antibody. When the glycodelin monoclonal antibodies of the present invention are used in the sandwich ELISA methods disclosed herein, any of the 2G7.1, 8G8.3, or 3A10.25 antibodies may be used as the capture or detector antibody. In one particular embodiment, the capture antibody is glycodelin monoclonal antibody 2G7.1 and the detector antibody is either the 8G8.3 or 3A10.25 antibody. The antibodies of the invention may be used in any assay format to detect glycodelin, including but not limited to multiplex bead-based assays, using the LUMINEX 200® platform or MAGPLEX® magnetic microbeads.

With respect to the sandwich ELISA format described above in which two antibodies for the same biomarker (i.e., glycodelin) are used, multi-step analyses may be performed to identify particular antibody combinations or pairings and concentrations of these antibodies that produce the best results with respect to complementarity of the antibodies and signal-to-noise ratios achieved with a particular combinations of antibodies, using routine methods known in the art for optimizing such results. In order to obtain optimal results in a sandwich ELISA format, the capture and detector antibodies should have distinct antigenic sites, as discussed above.

The methods of the invention find further use in monitoring the progression or regression of ovarian cancer. In one embodiment of the invention for monitoring the progression/regression of ovarian cancer, the method comprises testing a sample from the patient to determine the level of glycodelin in the patient body sample, determining the level of glycodelin in another sample from the patient at a later point in time, and comparing the glycodelin expression level at the earlier time point with that at the later time point, wherein a change in the level of glycodelin is indicative of the progression of the cancer in the patient. A decrease in glycodelin expression would be consistent with an improvement in the patient's condition. Similarly, the methods disclosed herein may be used to assess the efficacy of a particular ovarian cancer therapy or therapeutic regimen. For example, the method comprises testing a sample from the patient to determine the level of glycodelin in the patient body sample prior to initiation of an ovarian cancer therapy, administering the ovarian cancer therapy, determining the level of glycodelin in another sample from the patient during the time period of the therapy and/or following the completion of the therapy, and comparing the glycodelin expression level prior to initiation of the therapy and after therapy has started or has been completed, wherein a change in the level of glycodelin is indicative of the efficacy of the ovarian cancer therapy. A decrease in glycodelin expression would be consistent with the therapy being efficacious.

The efficacy of the methods disclosed herein may be assessed by calculating such values as sensitivity, specificity, positive predictive (PPV), and negative predictive value (NPV). As used herein, "specificity" refers to the proportion of disease negatives that are test-negative. In a clinical study, specificity is calculated by dividing the number of true negatives by the sum of true negatives and false positives. By "sensitivity" is intended the level at which a method of the invention can accurately identify samples that have been confirmed as positive (i.e., true positives). Thus, sensitivity is the proportion of disease positives that are test-positive. Sensitivity is calculated in a clinical study by dividing the number of true positives by the sum of true positives and false negatives. In some embodiments, the sensitivity of the disclosed methods for diagnosing ovarian cancer or for identifying patients with an increased likelihood of having ovarian cancer is at least about 70%, in other embodiments at least about 80%, and in still other embodiments at least about 90, 91, 92, 93, 94, 95, 96, 97, 98, 99% or more. Furthermore, the specificity of the present methods in some embodiments is at least about 70%, in other embodiments at least about 80%, and in still other embodiments at least about 90, 91, 92, 93, 94, 95, 96, 97, 98, 99% or more.

The term "positive predictive value" or "PPV" refers to the probability that a patient has the disease of interest (e.g., ovarian cancer) restricted to those patients who are classified as positive using a method of the invention. PPV is calculated in a clinical study by dividing the number of true positives by the sum of true positives and false positives. The "negative predictive value" or "NPV" of a test is the probability that the patient will not have the disease when restricted to all patients who test negative. NPV is calculated in a clinical study by dividing the number of true negatives by the sum of true negatives and false negatives.

Kits comprising at least one glycodelin monoclonal antibody of the invention are further provided. By "kit" is intended any manufacture (e.g., a package or a container) comprising at least one reagent, i.e., an antibody, for specifically detecting the expression of glycodelin. The kit may be promoted, distributed, or sold as a unit for performing the methods of the present invention. Furthermore, any or all of the kit reagents may be provided within containers that protect them from the external environment, such as in sealed containers. The kits may also contain a package insert describing the kit and or instructions for its use.

Kits for performing methods for detecting ovarian cancer and for identifying a patient with an increased likelihood of having ovarian cancer generally comprise at least one monoclonal antibody directed to glycodelin, chemicals for the detection of antibody binding, a counterstain, and, optionally, a bluing agent to facilitate identification of positive staining cells. Any chemicals that detect antigen-antibody binding may be used in the kits of the invention. For example, a secondary antibody that is conjugated to an enzyme that catalyzes the deposition of a chromogen at the antigen-antibody binding site may be provided. Such enzymes and techniques for using them in the detection of antibody binding are well known in the art. Chromogens compatible with the conjugated enzyme (e.g., DAB in the case of an HRP-labeled secondary antibody) and solutions, such as hydrogen peroxide, for blocking non-specific staining may be further provided. The kits may additionally comprise a peroxidase blocking reagent (e.g., hydrogen peroxide), a protein blocking reagent (e.g., purified casein), and a counterstain (e.g., hematoxylin). A bluing agent (e.g., ammonium hydroxide or TBS, pH 7.4, with TWEEN®-20 and sodium azide) may be further provided in the kit to facilitate detection of positive staining cells. Kits may also comprise positive and negative control samples for quality control purposes. Development of appropriate positive and negative controls is well within the routine capabilities of those of ordinary skill in the art.

Other kits of the invention for performing the sandwich ELISA methods described herein generally comprise a capture antibody, optionally immobilized on a solid support (e.g., a microtiter plate), and a detector antibody coupled with a detectable substance, examples of which are set forth herein above. In certain embodiments, the capture antibody and the detector antibody are monoclonal antibodies, particularly glycodelin monoclonal antibodies, more particularly the glycodelin monoclonal antibodies designated 2G7.1, 8G8.3, or 3A10.25. In one kit of the invention for practicing the sandwich ELISA method, the capture antibody is glycodelin monoclonal antibody 2G7.1, immobilized on a microtiter plate, and the detector antibody is HRP-labeled 8G8.3 or 3A10.25. Chemicals for detecting and quantitating the level of detector antibody bound to the solid support (which directly correlates with the level of glycodelin in the sample)

may be optionally included in the kit. Purified glycodelin may also be provided as an antigen standard.

In another embodiment, the kits of the invention comprise at least two glycodelin monoclonal antibodies, more particularly monoclonal antibodies 2G7.1 and either 8G8.3 or 3A10.25. Without intending to be limited to any particular assay format or methodology, as described below in the Experimental Section, glycodelin monoclonal antibodies 2G7.1 and either 8G8.3 or 3A10.25 have been shown to be a particularly useful combination of glycodelin monoclonal antibodies for the detection of purified glycodelin and ovarian cancer samples, more particularly in sandwich ELISA methods wherein the 2G7.1 antibody serves as the capture antibody and either the 8G8.3 or 3A10.25 antibody serves as the detector antibody. One of skill in the art will recognize that the capture and detector antibody may be "switched" in the sandwich ELISA format or that other antibodies may be used in the methods and kits of the invention, in addition to one or more of the glycodelin monoclonal antibodies disclosed herein. For example, antibodies to other biomarkers selectively overexpressed in ovarian cancer, including but not limited to HE4, CA125, MMP-7, Muc-1, PAI-1, CTHRC1, inhibin, PLAU-R, prolactin, KLK-10, KLK-6, and SLPI, alpha-1 anti-trypsin (AAT), Imp-2, FLJ0546, FLJ23499, MGC13057, SPON1, S100A1, SLC39A4, TACSTD2, MBG2, HETKL27 (MAL2), Cox-1, protein kinase C-iota, cadherin-6, ADPRT, matriptase, folate receptor, claudin 4, mesothelin, aquaporin 5, cofilin 1, gelsolin, clusterin, alpha tetranectin, vitronectin, pregnancy-associated plasma protein-A (PAPP-A), folistatin, B7-H4, YKL-40, claudin 3, Elafin, and KOP. Biomarkers of particular interest include but are not limited to HE4, CA125, MMP-7, Muc-1, PAI-1, CTHRC1, inhibin, PLAU-R, prolactin, KLK-10, KLK-6, SLPI, and alpha-1 anti-trypsin. When multiple antibodies are present in a kit of the invention, each antibody may be provided as an individual reagent or, alternatively, as an antibody cocktail comprising all of the antibodies of interest.

Although the above methods, antibodies, and kits for diagnosing ovarian cancer and for identifying patients with an increased likelihood of having ovarian cancer have been described herein in some detail, one of skill in the art will recognize that the disclosed methods and compositions could be similarly applied to other cancers or diseases in which glycodelin is overexpressed. One of skill in the art will further recognize that any or all of the steps in the methods of the invention could be implemented by personnel in a manual or automated fashion. Thus, the steps of sample preparation, antibody incubation, and detection of antibody binding may be automated.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation:

EXPERIMENTAL

Example 1

Production of Mouse Monoclonal Antibodies to Glycodelin

Recombinant antigen immunization strategies were undertaken to generate mouse monoclonal antibodies specific for glycodelin. The immunogenic polypeptide used to produce the mouse glycodelin monoclonal antibodies comprised the glycodelin sequence (SEQ ID NO:1) fused to a small polypeptide linker and a carboxy-terminal hexahistidine tag. The sequence of the glycodelin immunogenic polypeptide is set forth in SEQ ID NO:4. The immunogenic glycodelin polypeptide was overexpressed in a HEK (human embryonic kidney) cell line that contains the nucleic acid encoding the Epstein-Barr Nuclear Antigen, and the hexahistidine-tagged glycodelin protein was purified from the media fraction using a chelating agarose charged with Ni+2 ions (Ni-NTA, Qiagen Inc.).

Mice were then immunized with the purified glycodelin protein and lymphocyte fusions were accomplished by performing Repetitive Immunizations Multiple Sites technology (RIMMS), essentially as described in Kilpatrick et al (1997) *Hybridoma* 16(4):381-389; Wring et al. (1999) *J. Pharm. Biomed. Anal.* 19(5):695-707; and Bynum et al. (1999) *Hybridoma* 18(5):407-411, or by conventional immunizations, as well known in the art. Antibody-producing cells were isolated from the immunized mice and fused with myeloma cells to form monoclonal antibody-producing hybridomas. Primary screening of hybridoma supernatants was performed using recombinant glycodelin protein and routine Western blot techniques well known in the art to confirm binding to glycodelin. In addition, affinity assays were performed to enhance the selection of specific glycodelin antibodies. The glycodelin antibodies of the invention are optimally monoclonal antibodies, as they were obtained from a population of substantially homogeneous antibodies by limiting dilution cloning.

Specific glycodelin monoclonal antibodies of interest were selected and purified from the culture media supernatants of the hybridoma cells using recombinant Protein A-coated resin (MABSELECT SURE®, GE Healthcare). Purified antibodies were subjected to further characterization. Glycodelin monoclonal antibodies 2G7.1, 8G8.3, and 3A10.25 were determined to be of the IgG$_1$ isotype. Details of the epitope mapping of these antibodies are described below.

Example 2

General Method for Epitope Mapping

General Approach

Epitope mapping was performed essentially as described in U.S. Patent Application Publication No. 2006/0252106 to identify the linear or non-linear, discontiguous amino acid sequence within an antigenic protein (i.e., the epitope in, for example, glycodelin) that is recognized by a particular monoclonal antibody. A general approach for epitope mapping requires the expression of the full-length protein, as well as various fragments (i.e., truncated forms) of the protein, generally in a heterologous expression system. These various recombinant proteins are then used to determine if the specific monoclonal antibody is capable of binding one or more of the truncated forms of the target protein. Through the use of reiterative truncation and the generation of recombinant proteins with overlapping amino acid regions, it is possible to identify the region that is recognized by the monoclonal antibody under investigation. Western blot analysis, ELISA, or immunoprecipitation is employed to determine if the specific monoclonal antibody under investigation is capable of binding one or more of the recombinant protein fragments. This approach can ultimately identify the peptide regions that contains the epitope and, in some cases, to refine the epitope precisely to an approximately 5-15 amino acid sequence. An epitope can be a continuous linear sequence approximately 5-15 amino acids in length, nonlinear (e.g., discontinuous with the antibody binding to a site on the protein composed of different sections of the peptide chain), or both linear and nonlinear epitope.

Systematic techniques for identifying epitopes are known in the art, and one general approach requires expression of the full length protein as well as various fragments (i.e., truncated forms) of the protein, generally in a heterologous expression system (e.g., RTS System, "Rapid Translation System" Roche Applied Science). The recombinant proteins, fused with an N-terminal protein (e.g., GFP), are then used to determine if the specific monoclonal antibody is capable of binding one or more of the truncated forms of the glycodelin protein. Through the use of reiterative truncation and generation of recombinant proteins with overlapping amino acid regions, and by Western blot, ELISA, and/or immunoprecipitation methods, it is possible to identify the region that is recognized by the monoclonal antibody under investigation. Characterization of the Epitopes of Glycodelin Monoclonal Antibodies 2G7.1, 8G8.3, and 3A10.25

Epitope mapping for glycodelin monoclonal antibodies 2G7.1, 8G8.3, and 3A10.25 was carried out essentially via the iterative process described above. Further mapping was performed using CLIPS™ (chemically-linked immunogenic peptides on scaffolds) technology, available from Pepscan Presto, was used to map the conformational epitopes, wherein various glycodelin peptides were chemically linked in order to produce synthetic scaffold peptides that mimic complex protein structures (e.g., secondary and tertiary structures) and juxtapose non-adjacent regions of the glycodelin polypeptide to reconstruct the discontinuous epitope. See, for example, Timmerman et al. (2009) *Open Vaccine J* 2:56-67; Meloen et al. (1997) Epitope mapping by PEPSCAN. In: Immunology Methods Manual, Ed. Iwan Lefkovits, Academic Press, pp 982-988; and the Pepscan Presto website available on the world wide web at pepscanpresto.com, each of which is herein incorporated by reference in its entirety. These synthetic scaffold peptides were analyzed by immunoassays for binding to each monoclonal antibody. Alanine-scanning mutagenesis (see, for example, Cunningham and Wells (1989) *Science* 244: 1081-1085) of the regions highlighted by the CLIPS™ analysis, in combination with immunoassays to measure the effects of the mutations on antibody binding, allowed for the identification of those residues that are important for the recognition of the glycodelin monoclonal antibodies designated as 8G8.3, 3A10.25, and 2G7.1.

Initial studies using the iterative process described above identified the epitope of the monoclonal antibody designated as 2G7.1 as ATLLDTDYDNFLFLCLQDTTT PIQSMMC-QYL (SEQ ID NO:3; corresponding to residues 110 through 140 of the full-length glycodelin amino acid sequence set forth in SEQ ID NO:1). The CLIPS™ analysis and alanine-scanning mutagenesis indicated that the most important sequence needed for binding of the 2G7.1 antibody to glycodelin was the PIQS sequence (SEQ ID NO:5; corresponding to residues 131 through 134 of SEQ ID NO:1). In addition, the RFLP (SEQ ID NO:6; corresponding to residues 159 through 162 of SEQ ID NO:1) and LMATLKAPL (SEQ ID NO:7; corresponding to residues 49 through 57 of SEQ ID NO:1) sequences are also important for full binding of 2G7.1. This suggests that monoclonal antibody 2G7.1 is capable of recognizing a linear epitope (SEQ ID NO:3 and 5), but the full epitope comprises discontinuous sequences.

The epitopes for the glycodelin monoclonal antibodies designated as 8G8.3 and 3A10.25 were determined to be conformational epitopes. The epitope of both the 8G8.3 and 3A10.25 antibodies is dependent upon the presence of the two cysteine residues found at amino acid residue positions 84 and 178 of SEQ ID NO:1, which likely form a disulfide bridge. Further, conformational surfaces formed by residues LMATLKAPL (SEQ ID NO:7; corresponding to residues 49 through 57 of SEQ ID NO:1), RWENNSCVE (SEQ ID NO:8; corresponding to residues 78 through 86 of SEQ ID NO:1), PIQS (SEQ ID NO:5; corresponding to residues 131 through 134 of SEQ ID NO:1), RPLP (SEQ ID NO:6; corresponding to residues 159 through 162 of SEQ ID NO:1), and KQMEEPCRF (SEQ ID NO:9, corresponding to residues 172 through 180 of SEQ ID NO:1) are important for antigen recognition for both the 8G8.3 and 3A10.25 antibodies. It should be noted that although the epitope for the 2G7.1 antibody partially overlaps with the epitope for the 8G8.3 and 3A10.25 antibodies, neither the 8G8.3 nor 3A10.25 antibody compete with the 2G7.1 antibody for binding to glycodelin.

Example 3

Sandwich ELISA Assay Utilizing Glycodelin Monoclonal Antibodies 2G7.1 and 8G8.3 to Detect Glycodelin in Ovarian Cancer in Patient Serum Samples The sandwich ELISA immunoassay was used to detect glycodelin in sera from ovarian cancer patents and ovarian cancer-free patients. The capture antibody used in this set of experiments, the 2G7.1 glycodelin antibody, was bound to a microtiter plate well by passive absorption. The 8G8.3 antibody was used as the detector antibody and was labeled with a horseradish peroxidase (HRP) for detection of antigen-antibody binding. The patient sera samples were analyzed using the sandwich ELISA technique, essentially as described above, to measure glycodelin levels in sera from a patient cohort of 91 ovarian cancer patients, at various stages of the disease, and 89 "normal" patients not suffering from ovarian cancer. Specifically, the chromagen tetramethylbenzidine (TMB) was added, and optical density (OD) at 450 nm was determined. A cut-off threshold of glycodelin expression, as determined by the OD for the samples, of two standard deviations from the mean glycodelin expression level was obtained from the cohort of 58 "normal" serum samples (i.e., from patients not suffering from ovarian cancer). Glycodelin expression levels above the threshold value were deemed "positive," whereas those below the threshold level were considered "negative." The test cohort further consisted of 60 ovarian cancer serum samples Stages 1, 2, 3, and 4) and 18 benign serum samples (i.e., serum samples from patients with nonmalignant, noncancerous pelvic masses).

Results

Overall, analysis of glycodelin expression using the sandwich ELISA demonstrated a high specificity of 92% and a sensitivity of 50% in differentiating ovarian cancer samples from the normal, non-cancerous samples. Specifically within each stage of ovarian cancer, this method resulted in sensitivities of 37.5% (Stage 1; 3/8), 38.9% (Stage 2; 7/18), 80% (Stage 3; 12/15), and 40% (Stage 4; 2/5).

Example 4

Figure 1B:
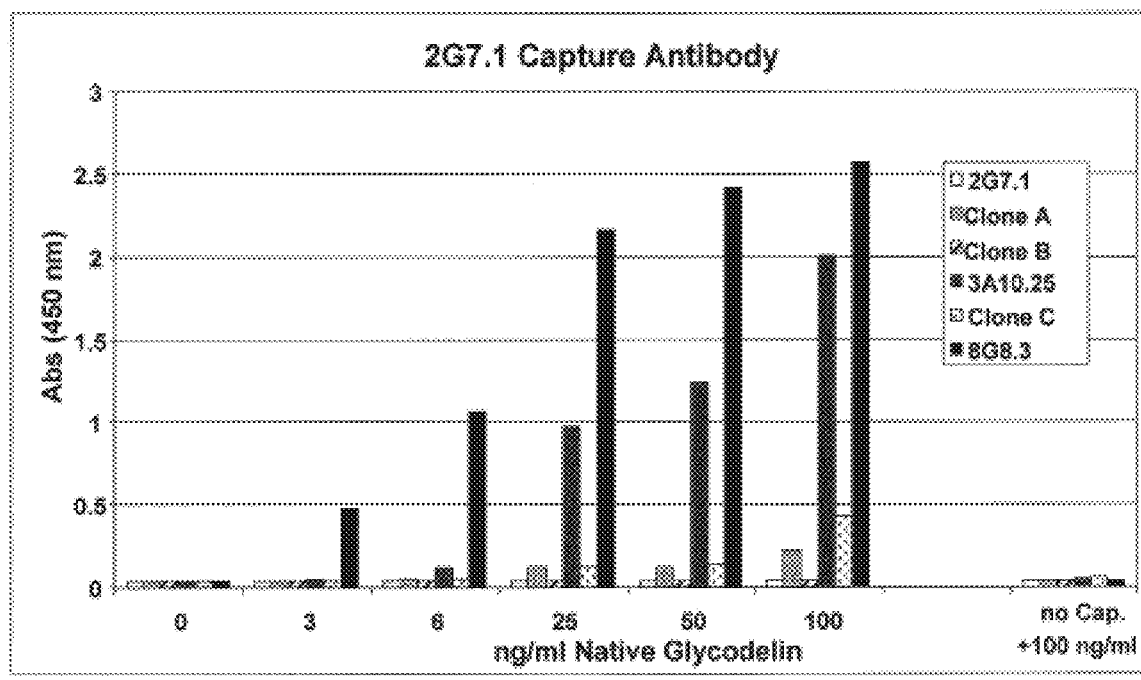
FIG. 1B provides the results obtained with increasing concentrations of native glycodelin as the "target" antigen. Experimental details are set forth in Example 4.

Assay to Identify Preferred Pairs of Monoclonal Glycodelin Antibodies for Use in the Sandwich ELISA Format Analyses were performed to identify preferred complementary pairings of glycodelin monoclonal antibodies for use in sandwich ELISA immunoassays. Specifically, the 2G7.1 glycodelin antibody was bound to a microtiter plate well by passive absorption and used as the capture antibody in this set of experiments. Various glycodelin antibodies, including 8G8.3 and 3A10.25 and other glycodelin antibodies designated only as, for example, "Clone A," were assayed as the detector antibody in the sandwich ELISA using varying amounts of recombinant or native glycodelin as the "target" antigen in a buffer comprising 1% BSA/PBS/TWEEN®-20. Each detector antibody was labeled with HRP and the chromagen TMB was used for detection of antigen-antibody binding by measuring OD at 450 nm. The results obtained in the sandwich ELISA with recombinant glycodelin and native glycodelin are set forth in FIGS. 1A and 1B, respectively. These figures demonstrate that the use of the 2G7.1 glycodelin antibody as the capture antibody and either the 8G8.3 or 3A10.25 antibody as the detector antibody successfully detected recombinant and native glycodelin in a dose-dependent manner. A higher signal relative to that observed with the other glycodelin detector antibodies analyzed than was obtained with either the 8G8.3 or 3A10.25 antibody was used to detect native glycodelin protein. See FIG. 1B.

Example 5

Combined Assessment of CA125 and Glycodelin Expression to Provide a More Accurate Ovarian Cancer Diagnosis A cohort of serum samples consisting of 150 benign, 76 ovarian cancer, 17 borderline, and 11 interfering pathology samples was analyzed by both traditional CA125 analysis as known in the art and the sandwich ELISA utilizing the glycodelin antibodies described herein. The sandwich ELISA methods were performed essentially as described above in Example 3. An increased predictive value was observed in women over the age of 55 via the glycodelin antibody sandwich ELISA relative to CA125 testing alone. Specifically, the increased predictive value corresponds to nine patients that were accurately identified as having ovarian cancer out of the thirty patients that were classified as negative by CA125 testing alone. That is, the glycodelin antibodies disclosed herein were able to accurately identify a percentage of patients deemed negative by assessment of CA125 serum levels alone (i.e., the glycodelin antibodies helped decrease the number of "false negatives" with CA125 testing alone). These experiments indicate that detection of glycodelin may significantly improve the identification of patients with ovarian cancer at an earlier stage of the disease and improve clinical management of the disease.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A monoclonal antibody that is capable of specifically binding to glycodelin, wherein the antibody is selected from the group consisting of:
   (a) the monoclonal antibody produced by the hybridoma cell line 2G7.1, deposited with the ATCC as Patent Deposit No. PTA-9684;
   (b) the monoclonal antibody produced by the hybridoma cell line 8G8.3, deposited with the ATCC as Patent Deposit No. PTA-9685;
   (c) the monoclonal antibody produced by the hybridoma cell line 3A10.25, deposited with the ATCC as Patent Deposit No. PTA-9686;
   (d) a monoclonal antibody that binds to an epitope capable of binding the monoclonal antibody produced by the hybridoma cell line 2G7.1, 8G8.3, or 3A10.25;
   (e) a monoclonal antibody that competitively interferes in a competitive binding assay with the monoclonal antibody produced by the hybridoma cell line 2G7.1, 8G8.3, or 3A10.25; and,
   (f) a monoclonal antibody that is an antigen binding fragment of a monoclonal antibody of (a)-(e), wherein the fragment retains the capability of specifically binding to glycodelin.

2. The monoclonal antibody of claim 1, wherein said monoclonal antibody binds to the glycodelin epitope sequence set forth in SEQ ID NO:3.

3. The monoclonal antibody of claim 1, wherein said monoclonal antibody binds to a glycodelin epitope sequence comprising the sequence set forth in SEQ ID NO:5 at the amino acid residue positions corresponding to positions 131 through 134 of SEQ ID NO:1, the sequence set forth in SEQ ID NO:6 at the amino acid residue positions corresponding to positions 159 through 162 of SEQ ID NO:1, and the sequence set forth in SEQ ID NO:7 at the amino acid residue positions corresponding to positions 49 through 57 of SEQ ID NO:1.

4. The hybridoma cell line 2G7.1, deposited with the ATCC as Patent Deposit No. PTA-9684.

5. The hybridoma cell line 8G8.3, deposited with the ATCC as Patent Deposit No. PTA-9685.

6. The hybridoma cell line 3A10.25, deposited with the ATCC as Patent Deposit No. PTA-9686.

7. A hybridoma cell line capable of producing a monoclonal antibody of claim 1.

8. A kit for diagnosing ovarian cancer in a patient or for identifying patients with an increased likelihood of having ovarian cancer comprising:
   a) a capture antibody immobilized on a solid support, wherein the capture antibody is the monoclonal antibody produced by the hybridoma cell line 2G7.1, deposited with the ATCC as Patent Deposit No. PTA-9684; and
   b) a detector antibody that is labeled with a detectable substance, wherein the detector antibody is the monoclonal antibody produced by the hybridoma cell line 8G8.3, deposited with the ATCC as Patent Deposit No. PTA-9685, or the monoclonal antibody produced by the hybridoma cell line 3A10.25, deposited with the ATCC as Patent Deposit No. PTA-9686.

9. The kit of claim 8, wherein the detector antibody is labeled with a detectable substance selected from the group consisting of horseradish peroxidase, alkaline phosphatase, β-galactosidase, acetylcholinesterase, streptavidin/biotin, avidin/biotin, umbelliferone, fluorescein, fluorescein isothiocyanate, rhodamine, dichlorotriazinylamine fluorescein, dansyl chloride, phycoerythrin, luminol, luciferase, luciferin, aequorin, a radioactive substance, digoxigenin, and quantum dots.

10. The kit of claim 8, wherein the solid support is selected from the group consisting of a cell culture plate, a microtiter cell culture plate well, a bead, a magnetic microbead, a cuvette, and a nanoparticle.

11. The kit according to claim 8 further comprising a positive control sample.

12. The kit according to claim 8 further comprising a negative control sample.

13. The kit according to claim 8 further comprising chemicals for detection of antibody-antigen binding.

14. The kit according to claim 8 further comprising instructions for use.

15. A kit for diagnosing ovarian cancer or for identifying patients with an increased likelihood of having ovarian cancer comprising at least one monoclonal antibody according to claim 1.

16. The kit of claim 15, wherein the monoclonal antibody is the monoclonal antibody produced by the hybridoma cell line 2G7.1, deposited with the ATCC as Patent Deposit No. PTA-9684, the monoclonal antibody produced by the hybridoma cell line 8G8.3, deposited with the ATCC as Patent Deposit No. PTA-9685, or the monoclonal antibody produced by the hybridoma cell line 3A10.25, deposited with the ATCC as Patent Deposit No. PTA-9686.

17. The kit of claim 15 comprising at least two antibodies selected from the group consisting of the monoclonal antibody produced by the hybridoma cell line 2G7.1, deposited with the ATCC as Patent Deposit No. PTA-9684, the monoclonal antibody produced by the hybridoma cell line 8G8.3, deposited with the ATCC as Patent Deposit No. PTA-9685, and the monoclonal antibody produced by the hybridoma cell line 3A10.25, deposited with the ATCC as Patent Deposit No. PTA-9686.

18. The kit of claim 15 comprising at least three antibodies selected from the group consisting of the monoclonal antibody produced by the hybridoma cell line 2G7.1, deposited with the ATCC as Patent Deposit No. PTA-9684, the monoclonal antibody produced by the hybridoma cell line 8G8.3, deposited with the ATCC as Patent Deposit No. PTA-9685, and the monoclonal antibody produced by the hybridoma cell line 3A10.25, deposited with the ATCC as Patent Deposit No. PTA-9686.

* * * * *